United States Patent [19]

Kratochvil et al.

[11] Patent Number: 4,533,456
[45] Date of Patent: Aug. 6, 1985

[54] OXYGEN SENSOR FOR RAPID BLOOD GAS ANALYSIS

[75] Inventors: Jiri Kratochvil, Sandy; Jiri Janata, Salt Lake City, both of Utah

[73] Assignee: Critikon, Tampa, Fla.

[21] Appl. No.: 597,001

[22] Filed: Apr. 5, 1984

[51] Int. Cl.³ .......................................... G01N 27/46
[52] U.S. Cl. .................................... 204/415; 204/1 T; 204/409
[58] Field of Search .............. 204/1 T, 1 P, 402, 415, 204/409

[56] References Cited

U.S. PATENT DOCUMENTS

| | | | |
|---|---|---|---|
| 3,493,485 | 2/1970 | MacArthur | 204/1 P |
| 3,556,950 | 1/1971 | Dahms | 204/411 |
| 3,718,562 | 2/1973 | Haddad | 204/415 |
| 3,997,420 | 12/1976 | Buzza | 204/420 |
| 4,003,705 | 1/1977 | Buzza et al. | 204/415 |
| 4,013,413 | 3/1977 | Stewart et al. | 436/53 |
| 4,022,575 | 5/1977 | Hansen et al. | 436/52 |
| 4,024,042 | 5/1977 | Enfors et al. | 204/415 |
| 4,149,949 | 4/1979 | Buzza et al. | 204/415 |
| 4,170,523 | 10/1979 | Buzza et al. | 204/401 |
| 4,172,770 | 10/1979 | Semersky et al. | 204/415 |
| 4,177,677 | 12/1979 | Ruzicka et al. | 422/82 |
| 4,224,033 | 9/1980 | Hansen et al. | 436/53 |
| 4,227,973 | 10/1980 | Ruzicka et al. | 204/1 T |
| 4,248,712 | 2/1981 | Bauermeister | 204/415 |
| 4,293,307 | 10/1981 | Simpson et al. | 204/415 |
| 4,314,824 | 2/1982 | Hansen et al. | 436/52 |
| 4,315,754 | 2/1982 | Ruzicka et al. | 73/61.1 C |

OTHER PUBLICATIONS

Nord et al., "Extraction Based on the Flow-Injection Principle", Part 5, *Analytica Chimica Acta*, 118, (1980), 285-292.

van Kemper et al., "Alternative Methods of $CO_2$ Measurement, with Particular Reference to Continuous Recording", *National Bureau of Standards Special Pub. 450, Proceedings of a Workshop on pH & Blood Gases, etc.*, Issued Jun. 1977.

Svenson et al., "Rapid Determination of Ammonia in Whole Blood & Plasma Using Flow Injection Analysis", *Clinica Chimica Acta*, 119, (1982), 7-14.

*Primary Examiner*—T. Tung
*Attorney, Agent, or Firm*—Audley A. Ciamporcero, Jr.

[57] ABSTRACT

In systems for rapid sequential analysis of fluid samples, such as blood samples, an electrochemical sensor is capable of equally rapid, sequential sample response by avoiding the need for equilibration during the measuring phase, and by substantially replacing the electrolyte acceptor for each sample. The sensor is made up of a pair of electrodes, an electrolyte acceptor, and a gas permeable membrane separating the electrolyte from the sample stream. Samples are passed rapidly by the membrane, and at the end of each such pass, the electrodes are polarized for a certain period, the flow of electrical current is measured, and the electrolyte is flushed and replaced by new electrolyte. This membrane material can be hydrophobic and also hydrophilic in nature.

3 Claims, 4 Drawing Figures

OXYGEN SENSOR FOR RAPID BLOOD GAS ANALYSIS

FIELD OF THE INVENTION

This invention relates to oxygen sensors, and more particularly to such sensors which are adapted to fast sample analysis systems, such as flow injection analysis systems.

BACKGROUND OF THE INVENTION

The principles of electrochemical sensors are well-known and are often applied to blood gas analysis and the like. Typically, these sensors incorporate a pair of electrodes extending into an electrolyte (also referred herin to as an "acceptor"), which is in turn separated from samples by a gas permeable membrane. Gases from the sample migrate across the membrane, are taken up selectively by the electrolyte—acceptor, and are electrochemically reduced at the electrodes. Based on calibration standards, the measured current corresponds linearly to the associated partial pressure of the gas in question. For example, if the electrodes respectively constitute a platinum cathode and a silver/silver chloride anode electrode having a constant voltage imposed thereon, the electrolyte acceptor solution is a bicarbonate buffer, and the membrane is one of several known membrane materials such as PTFE film, a $pO_2$ electrode results. Once such a cell equilibrates (i.e. partial pressure of oxygen concentration in the electrolyte acceptor is balanced with that in the sample), the electrical current across the electrodes is proportional to the oxygen partial pressure in the sample.

The principal drawbacks of electrochemical cells most frequently relate to their slow response time, their tendency to drift over passage of time, and the consequent need frequently to establish calibration standards. Objects of the present invention relate to reduction of the effect of these drawbacks.

An exciting new method of analysis has become popularly known as flow injection analysis (i.e. "FIA"). In accordance with the precepts of flow injection analysis, a sample slug is injected into a carrier stream, and passed through a flow cell which is penetrated by sensors of known response characteristics and desired selectivity. As the sample slugs pass each sensor, a selective reaction commences, and once the sample has passed by, the condition of the electrode is extrapolated or otherwise compared to known standards, to yield an indication of gas partial pressure, ion concentration, or the like element constituency in the sample. See, for example, U.S. Pat. Nos. 4,224,033 to Hansen et al.; 4,177,677 to Ruzicka et al.; 4,227,973 to Ruzicka et al.; 4,315,754 to Ruzicka et al.; 4,314,824 to Hansen et al.; 4,022,575 to Hansen et al.; and 4,013,413 to Stewart et al.

The flow injection analysis methodology provides the capacity for very rapid sequential analysis of successive samples, with the rate of successive sample analyses being limited in essence only by the inherent characteristics of the sensors used. For example, for many measurements, chemically sensitive field effect devices (i.e. those popularly known as "chemfet", "isfet", and "immunofet") show promise for instantaneous electrochemical response at least at the rates of presentation of FIA samples. Chemfet sensors will most likely not be suitable for all measurements, and indeed conventional pH, $pO_2$, $pCO_2$, and the like measurements may in the end be best made through conventional electrochemical sensors, or hybrid chemfet/conventional sensors. These sensors, however, tend to be rate limited by their need for equilibration, since their inherent operation involves at least partial saturation of the electrolyte-acceptor by the gases in question.

It is, therefore, a primary object of the present invention to provide electrochemical sensor designs and constructions which permit sequential sample analysis at rates such as those provided in flow injection analysis systems. It is an associated object to provide such sensors which are durable, inexpensive, and accurate for even very small sample volumes.

CROSS REFERENCE TO RELATED APPLICATION

Reference is made to concurrently filed copending U.S. application No. 597,002, of Ruzicka et al., commonly assigned and entiled "Sensor for Rapid Blood Gas Analysis" filed Apr. 5, 1984 and now abandoned. That application describes a sensor of construction similar to the one described herein, adapted for measurement of $pCO_2$ and pH.

SUMMARY OF THE INVENTION

The principles of the present invention are based on construction of a sensor which is integrated into the flow cell, and which permits evacuation and replacement of electrolyte acceptor fluid at least at the rate of presentation of successive samples to be analyzed. In accordance with the principles of the present invention, such a sensor comprises an oxygen permeable membrane to which samples are periodically exposed on one side, for example by direct passage thereacross in a FIA system. A reservoir for electrolyte acceptor is defined on the opposite side thereof, which in turn occupies a flow path for receipt of fresh fluid and exhaust of used fluid after samples have passed the membrane. Anode and cathode electrodes are immersed into or in contact with the electrolyte, that is, extending into the wall of the electrolyte reservoir. In accordance with the principles of the present invention, as the FIA sample passes on one side of the membrane, oxygen therefrom passes through the membrane and is taken up by the acceptor electrolyte. At this time, and for a time thereafter, the electrodes are electronically disconnected from one another. Still later, and after the sample has been removed, the electrodes are electrically connected and polarized by a predetermined voltage. An electrochemical reaction commences at the electrodes, and electrical current is established thereacross. A predetermined time after polarization, the current across the electrodes is measured and compared with prior calibration standards to yield an absolute evaluation of partial pressure of oxygen in the sample. Simultaneously, a flow of electrolyte is established at the respective input and output ports, whereby the "used" electrolyte is exhausted with the FIA sample and carrier, and the cell is charged with new fluid in anticipation of the next FIA sample.

In a preferred embodiment of the present invention, a $pO_2$ cell comprises respective cathode (platinum) and anode (silver/silver chloride) electrodes, and the electrolyte acceptor is a bicarbonate buffer. The gas permeable membrane is hydrophobic and effectively divides a single flow channel into two parts, one part of which is adapted to pass FIA carrier and samples, the other of which is adapted alternately to pass and hold predetermined quantities of electrolyte solution. Preferably, therefore, mutually controlled separate pumping schemes will be employed for the FIA and electrolyte subsytems. Switch means selectively connects the electrodes. Initially, at least two, and preferably three reference standards are passed through the FIA system, at a predetermined rate such that each sample is separately measured in the cell by like procedures. This sets up a standard against which unknowns will later be compared, to evaluate actual gas partial pressure in the unknown samples to be analyzed. Thereafter, at a fixed periodicity, slugs of FIA sample are passed through the cell, during passage of each of which oxygen migrates into the electrolyte acceptor. During this time and for a fixed period thereafter, the electrodes are unpolarized. Then, for another fixed period they are polarized. Then, the current is read and correlated with the standards to yield partial oxygen pressure in the sample. Finally, the electrolyte pumping system is activated, the "used" electrolyte acceptor in the cell is exhausted, and new electrolyte acceptor is provided prior to delivery of the next sample.

Features of the present invention therefore include sensitivity, durability, rapid rate of response, and inexpensive construction.

BEST MODE FOR CARRYING OUT THE INVENTION

It is to be emphasized that the principles of the present invention relate to design and construction of a sensor suitable for inclusion in flow injection analysis systems. The principles of the present invention do not embrace the flow injection analysis systems themselves. Hence, the instant disclosure provides adequate information for incorporating sensors in accordance with the principles of the present invention into FIA systems, and for operating those sensors in such systems. Reference may be had to the above-cited Hanssen and Ruzicka patents, and to the extensive literature which is available, for construction and use of an optimal FIA system. Further, to the extent that such might be required to complete the disclosure herein, the above-cited FIA patents are incorporated by reference herein.

Figure 1:
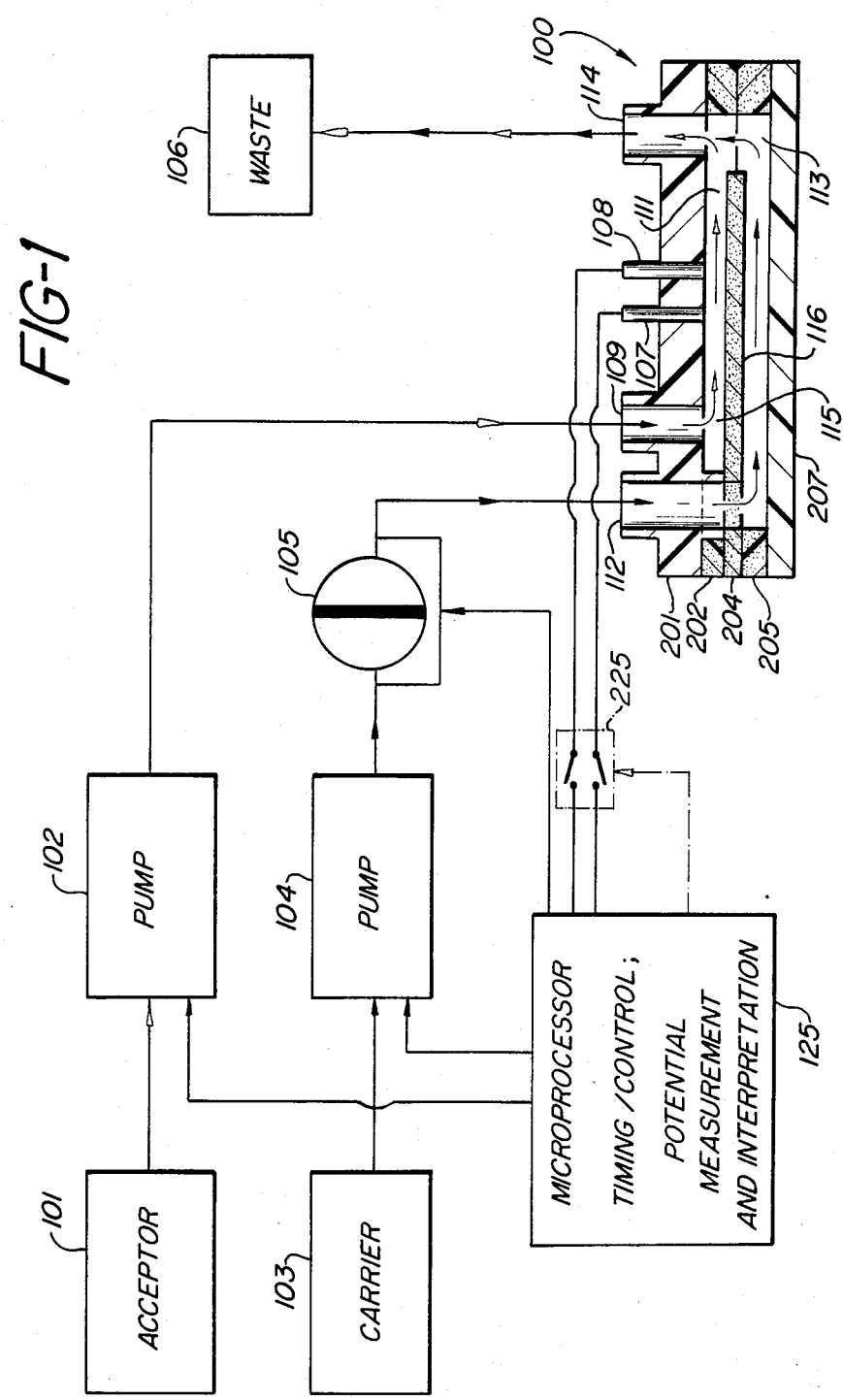
FIG. 1 shows in symbolic form the employment of the principles of the present invention, showing an exemplary symbolic flow cell in cross-section, and associated pumping systems for incorporating the sensor into a flow injection analysis system.

Referring first to FIG. 1, there is shown a symbolic setup for incorporation of a sensor in accordance with the principles of the present invention into a FIA system. A flow cell 100 defines both a passageway for FIA carrier and samples, between input port 112 and output port 113, and for electrolyte acceptor material between an input port 109 and an output port 111. In turn, the exhausted samples, carrier, and acceptor are discharged via a flow cell output 114 to an appropriate waste receptacle 106. Accordingly, a supply of acceptor 101 is drawn upon by a pump 102, under suitable timing control, to deliver acceptor material to the input port 109. The FIA aspect of the system comprises a supply of carrier, which is delivered via pump 104 to a sample injection valve 105, and thence to the FIA input port 112. The sensor of FIG. 1 is a $pO_2$ sensor, and accordingly includes a cathode electrode 107 and an anode electrode 108. For such a sensor, the acceptor fluid will preferably be a bicarbonate buffer solution.

A membrane 116 separates the FIA pathway from the acceptor reservoir 115, and hence defines the lower extremity of the sensor. Thus, depending whether the valve 105 has most recently been open or closed, fluid passing on the lower side of membrane 116 will either be the carrier solution from supply 103, or a slug of sample (e.g. 40 microliters in volume) introduced by the valve 105. As will be discussed in greater length hereinafter, although the FIA pathway constantly has fluid in motion, the acceptor stream has intermittent flow, with no fluid flow during times of measurement, interspersed with fluid flow at times of replacement of the acceptor fluid.

FIG. 1 including switch means 225, is shown to be under the general control of a microprocessor 125, which also controls the respective operation of pumps 102 and 104, and which gathers data from the electrodes 107 and 108 and in turn translates this data into useful format. In particular, the microprocessor control 125 operates the FIA system in accordance with the timing diagram set forth in FIG. 3. The interpretation of data from the electrodes 107 and 108 is likewise done in straightforward fashion, based on a table of values previously gathered and stored, for example by passage of at least two and preferably three reference standards through the cell prior to actual FIA measurement of unknown samples. Commercially available FIA systems, such as those which are available from Bifok AB, entail microprocessors of sufficient power and scope as to perform all the requisite operations, either inherently or with minor modification which is well within the scope of those of ordinary skill in the art.

Figure 2:
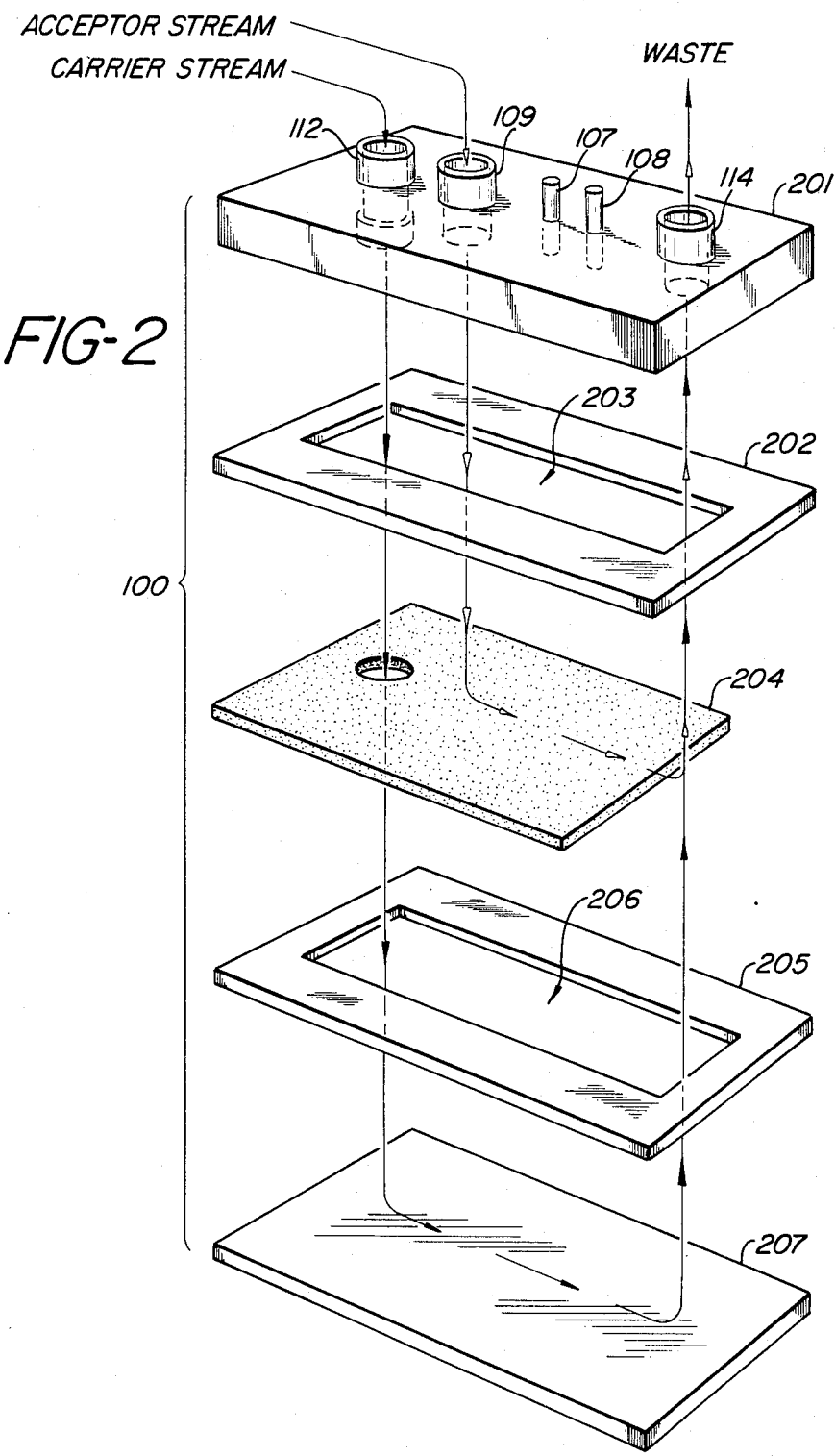
FIG. 2 shows an exploded component representation of a sensor in accordance with the principles of the present invention, integrated into a FIA flow cell.

Sensors in accordance with the principles of the present invention may perhaps be better understood upon consideration of FIG. 2, which shows an exploded version of an exemplary flow cell incorporating a sensor in accordance with the principles of the present invention. In essence, the cell and sensor construction is a "sandwich" which is easy and convenient to fabricate; it will be understood that those of ordinary skill in the art may in the end prefer to use more elaborate injection molding or the like techniques which will allow for economies of scale. The construction shown in FIG. 2, however, is the best mode contemplated by the inventors to date, and has been found to work satisfactorily. A lowermost plastic block, such as of polyvinylchloride, is penetrated by five separate openings, defining receptacles for the cathode and anode electrodes, 107 and 108 respectively, for the carrier stream input port 112, for the acceptor stream input port 109, and for the waste exhaust port 114. An acrylic adhesive material 202, having a channel 203 defined therein, overlays the lowermost PVC block 201. Next, a membrane 204, with an opening therein penetrated by the carrier stream port 112, overlies a predetermined portion of the channel 203 in the first layer of acrylic adhesive 202. Thereupon, a second layer of acrylic adhesive 205, with yet another channel 206 defined therein, overlies the membrane 204 and the lower acrylic adhesive portion 202. A plastic cover 207, for example also PVC, completes the arrangement. Thus, it will be seen that the membrane 204, together with the layers of acrylic adhesive 202 and 205, define the respective flow pathways for both the sample stream and the acceptor stream. In particular, it will be seen that the acceptor stream enters via input port 109, passes along the channel 203, and is exhausted via the waste port 114. The carrier stream enters via port 112, passes through the lower acrylic adhesive layer 202 and the opening in membrane 204, and then flows through channel 206 in the upper acrylic adhesive layer 205, and then out through the rightmost portion of lower acrylic adhesive 203 and to the waste exhaust port 114.

In preferred construction, the membrane 204 is made up of PTFE film, 0.0025 in thick, commercially available from DuPont Co. under the tradename "Teflon". Numerous membrane materials, known in the art to be suitable for electrochemical electrodes, however, will be applicable in accordance with the knowledge of those of ordinary skill.

In a preferred embodiment, the cathode electrode 107 is composed of platinum wire of 0.002 in. diameter, and anode electrode 108 is a conventional 0.02 in. diameter silver/silver chloride wire.

In preferred embodiments, the acrylic adhesive layers 202 and 205 are selected for their dimension (e.g. 125 microns thick), their dimensional stability, and their capacity both to bind the cell together and to define the pathways 203 and 206. A suitable formulation is commercially available from the 3M Corporation under the "3M" trademark, but these often have an acidic component therein. To the extent that this is so, it will be appropriate to presoak the cell in a Borax solution prior to use, thereby to neutralize the acidic component of the acrylic adhesive. It follows that acrylic adhesive compositions which have no such acidic component will not require such presoaking.

Figure 3:
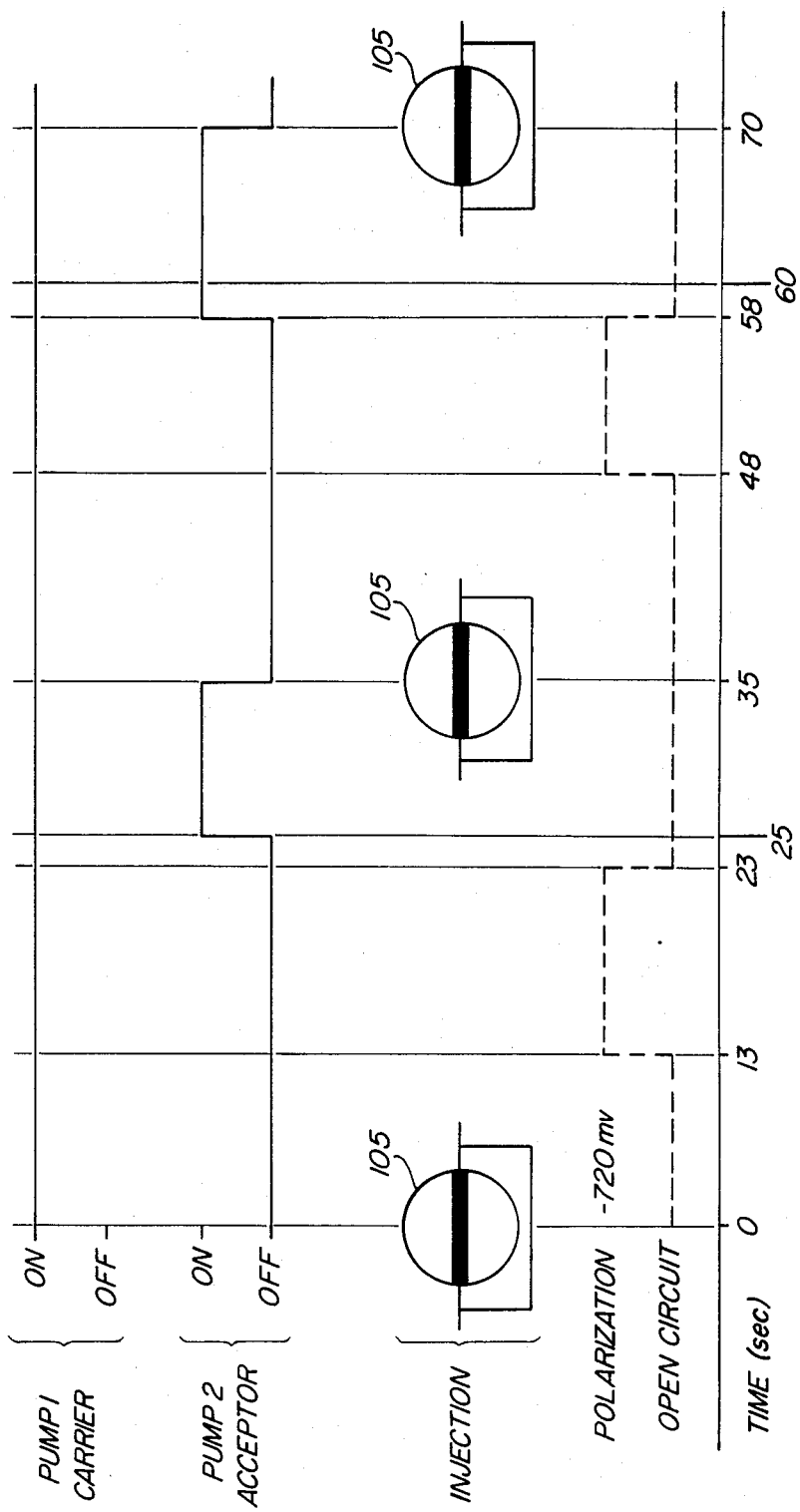
FIG. 3 shows a timing diagram illustrating use of a sensor in accordance with the principles of the present invention in a FIA-style system.

Referring to FIG. 3, there is shown an illustrative timing diagram whereby the principles of the present invention, configured generally as shown in FIG. 1, may be gainfully employed in conventional flow injection analysis systems. As stated hereinbefore, execution of procedures in accordance with FIG. 3 assumes presence of microprocessor capability from, or at least equivalent to, those available in commercially distributed FIA systems, such as those available from Bifok.

FIG. 3 is configured with passage of time represented, in seconds, from left to right. As shown in the top wave form, the first pump, providing flow injection analysis carrier, is constantly in an on condition, as shown by the steady state waveform. At the commencement of each cycle (which in the FIG. 3 embodiment is repeated at 35 second intervals), the sample injection valve 105 is brought on line (e.g. for 10 sec.), and a slug of sample passes into the carrier. At this time, the electrolyte acceptor pump 102 is disengaged, that is placed in the off condition, inasmuch as replacement of acceptor constituted one of the final steps of the preceding cycle. Significantly, as shown by the bottom waveform in FIG. 3, switches 225 are maintained in an open circuit condition at this time, that is, the anode 108 and cathode 107 electrodes have no polarization relative to one other. At exemplary flow rates, the full sample has passed the membrane portion of the system in approximately 10 seconds time, during all of which time oxygen from the sample was migrating across the membrane and was taken up by the acceptor.

When this has been completed, for example 13 seconds into the cycle, the switches 225 are closed, the anode 108 and cathode 107 electrodes stand polarized relative to one another (e.g. 720 m.v.), and an electrochemical reaction occurs in the acceptor as stimulated by the polarized electrodes. In fact, the mechanism of this reaction is conventional to prior art $pO_2$ sensors. A predetermined period, for example 10 seconds, is allowed for this reaction to continue, whereupon the current across the electrodes is measured (i.e. as a peak above the baseline defined by the polarization potential). The size of this peak above the baseline represents the oxygen tension in the sample most recently passed through the cell.

Figure 4:
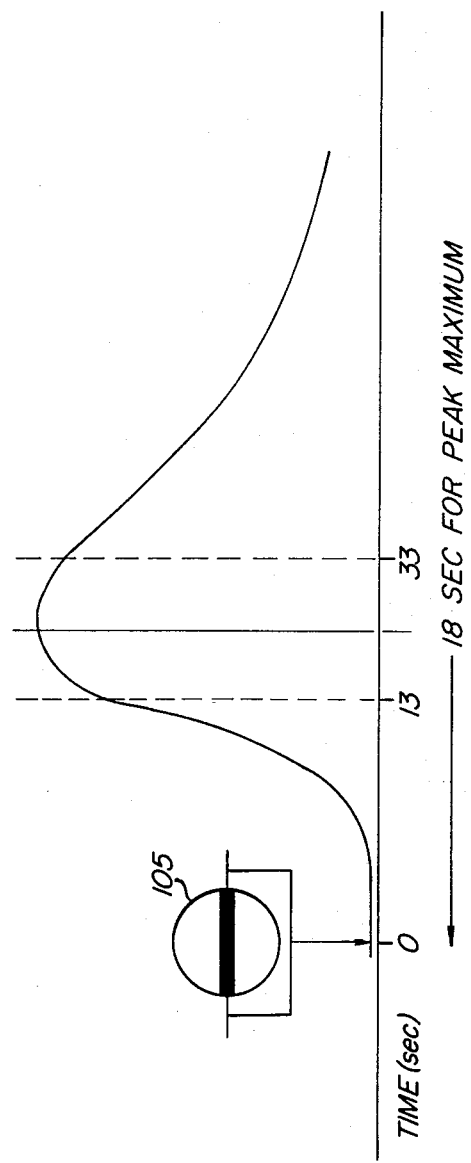
FIG. 4 shows an exemplary current measurement waveform consonant with operation pursuant to the method of FIG. 3.

Once the signal has been so processed, for example at the 23 second point as shown, the switches 225 are once more opened, and the active portion of the cycle is completed. Then, for example at the 25 second point, the acceptor pump 102 is actuated, and the used acceptor is discarded while a new supply of acceptor is furnished to the cell 100. At exemplary rates, this is completed in 10 seconds time, and at such point the acceptor pump is disengaged, and the system is prepared anew for processing of yet another sample. FIG. 3 shows sequential repetition of this sequence on a 35 second cycle. FIG. 4 represents an exemplary current waveform resulting from the electrochemical reaction.

It will be appreciated that the foregoing has set forth preferred and illustrative embodiments of the principles of the present invention. It is to be assumed, however, that those of ordinary skill in the relevant arts will develop numerous alternative formulations which nevertheless do not depart from the spirit or the scope of the present invention. Clearly, configurations of the various flow channels, reservoirs, and the like will no doubt be subject to the design talents of fluidics and molding specialists. Likewise, rates of response and constituency of materials will no doubt be improved by practitioners in the flow injection analysis as well as electrochemical sensor arts. Significantly, the current waveform shape is a function of sensor geometry and flow rate; hence, different geometries and flow rates will entail experimental determination of optimal timing sequences (of which FIG. 4 is an example). Finally, precise concentrations of solutions and formulations of membrane will progress with corresponding progress in those arts.

We claim:

1. In a system for analysis of partial pressures of gases in blood, an oxygen sensor comprising:
   (a) an oxygen permeable membrane to which blood samples are periodically exposed for a predetermined time period;
   (b) an electroylte acceptor for oxygen which passes through said membrane;
   (c) an anode electrode and a cathode electrode, which both are immersed in said electroyte; and the improvement which comprises
   (d) means for substantially replacing the electrolyte in said sensor prior to each presentation of respective samples to the other side of said membrane;
   (e) control means automatically operating a switch means for establishing an open circuit condition between said electrodes during replacement of said electrolyte and during and for a first predetermined time after presentation of each of said samples, and for polarizing said electrodes at a predetermined voltage for a second predetermined time; and (f) means for measuring current between said electrodes at the end of said second predetermined time.

2. A system as described in claim 1 wherein said first predetermined time is approximatley 13 sec., and said second predetermined time is approximately 10 sec.

3. A system as described in claim 2 wherein said anode is silver/silver chloride and said cathode is platinum.

* * * * *